United States Patent [19]

Gulbenk

[11] 4,028,092
[45] June 7, 1977

[54] SUBSTITUTED PYRIDINYLALKOXY-, PYRIDINYLALKYLSULFONYL- AND PYRIDINYLALKYLTHIOPHENYLUREA HERBICIDES

[75] Inventor: Alin H. Gulbenk, Walnut Creek, Calif.

[73] Assignee: The Dow Chemical Company, Midland, Mich.

[22] Filed: Oct. 14, 1975

[21] Appl. No.: 622,352

Related U.S. Application Data

[62] Division of Ser. No. 435,608, Jan. 22, 1974, Pat. No. 3,931,200.

[52] U.S. Cl. ..................................... 71/94; 71/74; 71/76
[51] Int. Cl.² ........................................ A01N 9/22
[58] Field of Search ................................... 71/94

[56] References Cited

UNITED STATES PATENTS

| | | | |
|---|---|---|---|
| 3,429,689 | 2/1969 | Duerr et al. | 71/94 |
| 3,576,616 | 4/1971 | Nowotny | 71/94 |
| 3,637,720 | 1/1972 | Nishiyama et al. | 260/297 R |

Primary Examiner—Lewis Gotts
Assistant Examiner—Catherine L. Mills
Attorney, Agent, or Firm—S. Preston Jones; Daniel L. DeJoseph

[57] ABSTRACT

Novel substituted pyridinylalkoxy-, pyridinylalkylsulfonyl- and pyridinylalkylthio- phenyl ureas and certain novel intermediates are provided. The compounds of the instant invention are useful as herbicides and can be formulated to provide herbicidal compositions.

15 Claims, No Drawings

SUBSTITUTED PYRIDINYLALKOXY-, PYRIDINYLALKYLSULFONYL- AND PYRIDINYLALKYLTHIOPHENYLUREA HERBICIDES

CROSS-REFERENCE TO RELATED APPLICATION

This is a division of application Ser. No. 435,608 filed Jan. 22, 1974, which is now U.S. Pat. No. 3,931,200, having issued Jan. 6, 1976.

CROSS-REFERENCE TO RELATED APPLICATION

This is a division, of application Ser. No. 435,608 filed Jan. 22, 1974 which is now U.S. Pat. No. 3,931,200, having issued Jan. 6, 1976.

SUMMARY OF THE INVENTION

The present invention is directed to substituted pyridinylalkyoxy-, pyridinylalkylsulfonyl- and pyridinylalkylthiophenylurea compounds corresponding to the formula:

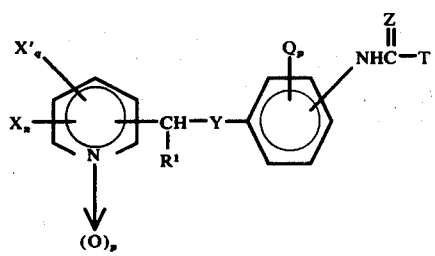

wherein

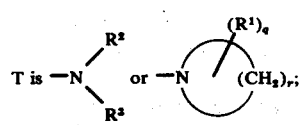

each X independently represents bromo, chloro, fluoro or iodo;
each X' independently represents trichloromethyl, $NH_2$, trifluoromethyl, cyano, methyl, methylthio or methoxy;
n represents an integer of 0 to 4, inclusive;
each q independently represents an integer of 0 to 2, inclusive;
each p independently represents an integer of 0 or 1;
r represents an integer of 4 or 5;
each $R^1$ is hydrogen or methyl;
Y is a chalcogen of atomic number 8 to 16, inclusive or $-SO_2$;
Q is methyl, ethyl or halo;
Z is a chalcogen of atomic number 8 to 16, inclusive;
$R^2$ represents hydrogen, alkyl of from 1 to about 4 carbon atoms, inclusive or an alkoxy group of from 1 to about 4 carbon atoms, inclusive; and
$R^3$ represents an alkyl group of from 1 to about 4 carbon atoms, inclusive.

The above substituent definition applies to the various formulas and reaction schemes hereinafter set forth.

DETAILED DESCRIPTION

The compounds of the present invention, hereinafter referred to as "active ingredients" are useful as herbicides, particularly as post-emergent herbicides. As used in the present specification and claims, the term "herbicide" means an active ingredient which, when used in a growth controlling amount, controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant germinant seeds, emerging seedlings, and established vegetation, including the roots and above-ground portions.

The term "alkyl" is used herein and in the appended claims to mean, unless otherwise specifically designated, a straight or branched-chain alkyl radical containing from 1 to about 4 carbon atoms, such as, for example, methyl, ethyl, propyl, isopropyl, butyl, isobutyl, and tert-butyl. The term "alkoxy" as employed designates a straight or a branched-chain radical containing from 1 to about 4 carbon atoms, such as, for example, methoxy, ethoxy, propoxy, isopropoxy, butoxy, isobutoxy and tert-butoxy.

The term "halo" and "halogen" are employed herein to represent chlorine, fluorine and bromine. The term "chalcogen" as used herein means those members of the recognized chalcogen group having an atomic number of 8 to 16, inclusive, i.e., oxygen and sulfur.

Preferred compounds of the present invention are those wherein q is at least one and n is zero. Another preferred class of compounds are those wherein q is 0 and n is at least 1. A further preferred class of compounds include those wherein n is 1, R is hydrogen and X is in the 6-ring position of the pyridine moiety. An additional preferred embodiment includes compounds wherein T is

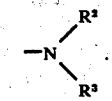

In still another preferred embodiment, T is

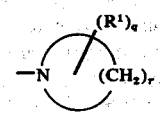

In yet another embodiment, T is

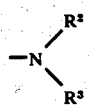

and $R^2$ and $R^3$ are both alkyl. An additional preferred class of compounds includes those wherein T is

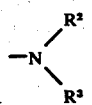

and $R^2$ is an alkoxy group.

The active ingredients of the present invention are prepared by a variety of methods. Novel intermediates wherein T is $R^3$ (i.e., alkyl of from 1 to about 4 carbon atoms), which are hereinafter referred to as "acetamide" compounds, can be prepared by reacting a selected substituted haloalkylpyridine reactant with a selected sodium acetamidophenate reactant in the presence of an inert solvent under reflux conditions. Such reaction can be represented schematically as follows:

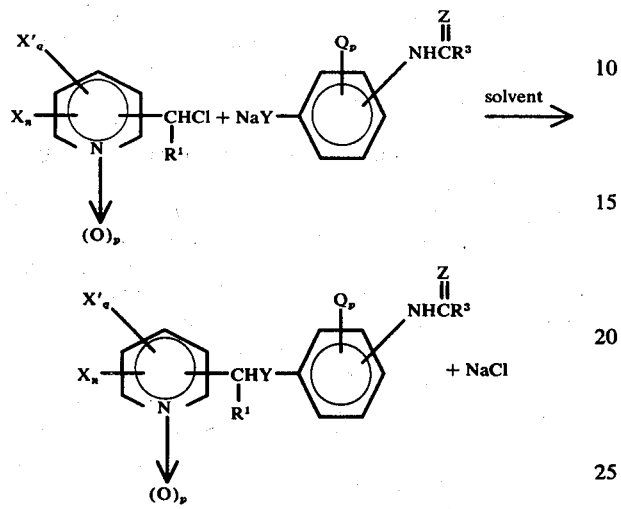

Reaction I

Reaction I proceeds readily under ambient atmospheric pressure at temperatures of from about 20° to about 75° C.

A solution of the sodium acetamidophenate reactant in an alcohol medium is added portionwise, ordinarily dropwise, to a solution of the substituted haloalkylpyridine reactant in an inert solvent such as, for example, dimethylsulfoxide, hexamethylphosphoramide, dimethylformamide, and the like. Stoichiometric proportions of the reactants are usually employed.

The sodium acetamidophenate solution, which can be prepared by rapidly adding stoichiometric proportions of acetamidophenol to a solution of sodium metal in dry methanol, is usually added dropwise to a well-stirred solution of haloalkylpyridine over a period of from about 30 to about 90 minutes. The reactants are usually mixed at ambient temperatures with the reaction proceeding exothermically. The reaction is maintained for a period of from about 1 to about 3 hours, after which the reaction mixture is distilled to remove the solvent, cooled, poured over ice and allowed to stand for a short period of time. The resulting product precipitate is recovered by filtration and recrystallized from a suitable solvent or solvent mixture, such as, for example, benzene, benzene/hexane, benzene/methylene chloride or the like.

Such acetamide intermediates are, with the exception of the N-oxide derivatives thereof in turn converted to a corresponding novel benzenamine intermediate which is employed in the preparation of certain active ingredients of the present invention wherein T is

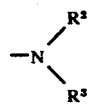

and $R^2$ is hydrogen or alkyl and Y is 0 or S. In such operations, the acetamide intermediates are treated with boron trifluoride in the presence of methanol, and the amine is reacted with an appropriated substituted (thio)-carbamoyl halide reactant, such as carbamoyl chloride, in the presence of pyridine to form the corresponding phenyl urea compounds. The reaction can be schematically represented as follows:

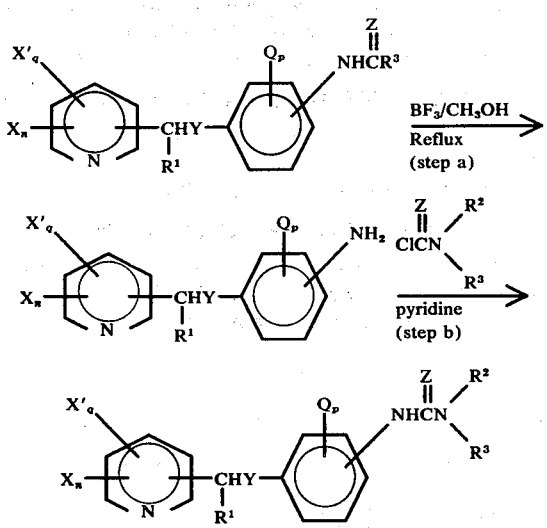

REACTION II

The reaction to convert the acetamide products to the corresponding amine intermediates (step a, Reaction II) proceeds readily under ambient atmospheric pressure and at the reflux temperature of the reaction mixture. In such operations, the acetamide product is mixed with a solution of borontrifluoride in methanol and the resulting reaction mixture is heated to the refluxing temperature of the mixture for a period of from about 1 to about 3 hours. An excess of borontrifluoride is usually employed. The methanol solvent is then usually distilled off and the concentrated reaction mixture is cooled, poured into cold water and treated with concentrated aqueous ammonia until the solution is basic. The resulting product precipitate is recovered by filtration, washed and recrystallized if desired from a solvent such as, for example, benzene, methylene chloride and the like. The aqueous filtrate remaining after recovery of the product precipitate can also be extracted with such solvents to recover additional quantities of the desired amine product.

The amine intermediates prepared above are, in step b of Reaction II, reacted with an appropriately substituted carbamoyl halide reactant in the presence of dry pyridine to obtain the desired phenyl urea compounds of the instant invention. The reaction proceeds readily under ambient temperature and pressure conditions. Generally, stoichiometric amounts of the reactants are employed. In carrying out the reaction, the total quantity of the carbamoyl halide reactant is usually added all at once to a solution of the amine reactant in pyridine and the resulting reaction mixture allowed to stand at ambient temperatures for a period of from about 12 to about 30 hours. The reaction mixture is then poured into cold water and allowed to stand for a period of time. The resulting product precipitate is recovered by filtration and mixed with a solvent, such as one of those hereinbefore mentioned. The resulting solvent-product solution is dried, treated with Norite, filtered and concentrated by evaporation to crystallize out the desired phenyl urea product.

The n-oxide derivatives of the above "phenylurea" compounds are usually prepared by other methods in view of the high reactivity of the N-oxide ($=N \rightarrow O$) group with certain reagents, such as the borontrifluoride reagent employed in step (a) of Reaction II. In such method, the salt of a selected substituted amino(-thio)phenol reactant of the formula:

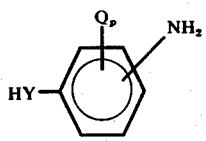

is reacted with the N-oxide derivative of a selected substituted haloalkylpyridine reactant to obtain the N-oxide form of the desired pyridinyloxy(thio)benzenamine intermediate. The latter reaction is carried out employing procedures analogous to those employed in Reaction I above. The benzenamine intermediate can thereafter be reacted with a carbamoyl halide reactant as in step (b) of Reaction II to obtain the desired N-oxide derivatives of the pyridinyl-(-alkoxy, -alkylthio, and -alkylsulfonyl)phenylurea compounds of the present invention.

In other procedures, the above amino(thio)phenol reactant can be reacted with a selected carbamoyl halide reactant, as in step (b) of Reaction II, to obtain a corresponding hydroxy- or mercapto- phenylurea reactant. The thus-obtained phenylurea reactant can be reacted with a haloalkylpyridine reactant or an N-oxide derivative thereof in the presence of a base, such as, for example, sodium metal in methanol, sodium hydroxide or the like, and a solvent carrier, such as previously mentioned herein, at temperatures ordinarily ranging from about 20° to about 80° C. or higher for a period generally from about 1 to about 6 or more hours. The desired N-oxide derivatives of the active ingredients of the invention are recovered in a manner similar to recovery procedures previously set forth.

The N-oxide derivatives of the haloalkylpyridine reactants employed above as starting materials are prepared according to conventional oxidative procedures. In typical known types of operations, the selected halopyridine reactant is treated with anhydrous trifluoroacetic acid and excess 90% hydrogen peroxide under reflux conditions to obtain the desired N-oxide derivative.

The novel benzenamine intermediates described above in relation to Reaction II, excluding the N-oxide derivatives thereof, can also be prepared in alternative procedures whereby a selected salt of a nitrophenol or -thiophenol is reacted with an appropriate substituted haloalkylpyridine compound to form the corresponding substituted nitrophenoxy- or nitrophenylthio- pyridine compound, which is then reduced to the corresponding aminophenoxy- or aminothiophenyl- pyridine compound with a reducing agent, such as iron powder. This reaction can be represented as follows:

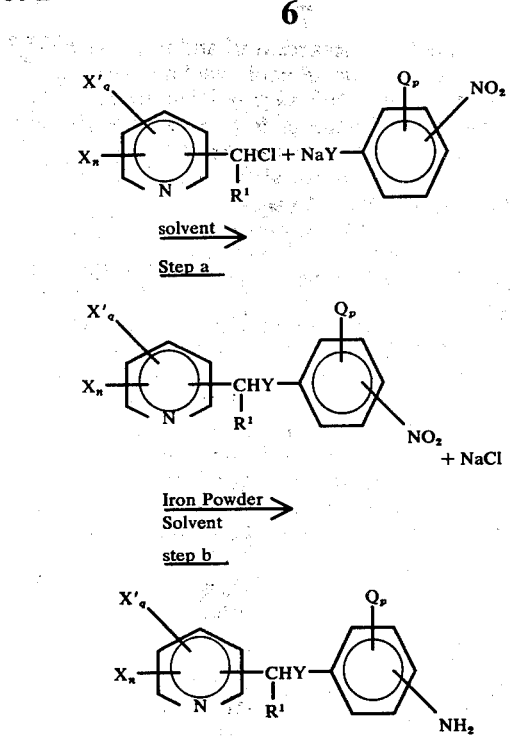

REACTION III

The reaction in step (a) of Reaction III proceeds readily under ambient atmospheric pressure at reaction temperatures of from about 100° to about 160° C. for a period of from about 3 to about 5 hours. In such operations, the salt of the substituted nitrophenol or nitrothiophenol is mixed with the selected haloalkylpyridine reactant in the presence of an inert solvent, such as previously mentioned with respect to Reaction I, and the resulting reaction mixture heated at a temperature within the above indicated ranges. Following the substantial completion of the reaction, the reaction mixture is cooled and mixed with cold water. The resulting product precipitate is recovered by filtration and recrystallized according to conventional techniques from a solvent such as, for example, benzene, methylene chloride and the like.

The product thus obtained from step (a) of Reaction III is mixed, in the presence of an aqueous alcohol solution, with a reducing agent, such as, for example, iron powder. The resulting reaction mixture is heated to the reflux temperature thereof with vigorous stirring and an alcohol solution of concentrated hydrochloric acid is added thereto, portionwise, over a 10 to 30 minute period. The reaction mixture is then heated at the reflux temperature for a period of from about 2 to about 4 hours and then filtered while hot. The solid product thus obtained is washed with an aqueous alkanol solution, such as 50–95% ethanol, and the filtrate portions combined and extracted with a solvent such as benzene, methylene chloride or the like. The extract is then dried, treated with activated charcoal, such as Norite, filtered and evaporated to dryness to obtain the desired amine intermediate product as a crystalline solid or oily liquid.

While a method of preparing N-oxide derivatives of the benzenamine intermediates has been previously described, such intermediates can also be prepared by first reducing a nitro(thio)phenol reactant to the corresponding amino(thio)phenol reactant with a reducing agent as in step (b) of Reaction III and then reacting a salt of such amino(thio)phenol reactant with an N-oxide derivative of a haloalkylpyridine reactant employing procedures analogous to those set forth in Reaction I. Such alternative procedures are employed in this instance in view of the high reactivity of the N-oxide group with a reducing agent.

Other phenyl urea compounds of the present invention, particularly wherein $R^2$ is alkoxy and $R^3$ is alkyl, can be prepared by reacting a selected substituted haloalkylpyridine with the salt of an amino(thio)phenol reactant to form a corresponding novel pyridinyl alkoxy- or pyridinylalkylthio- benzenamine intermediate (hereinafter "amine intermediate"), reacting said amine intermediate with phosgene or thiophosgene to form a corresponding novel pyridinylalkoxy- or pyridinylalkylthio- iso(thio)cyanate intermediate (hereinafter "iso(thio)cyanate intermediate") and reacting said iso(thio)cyanate intermediate with a selected substituted hydroxyl amine salt reactant as illustrated in the following reaction sequence:

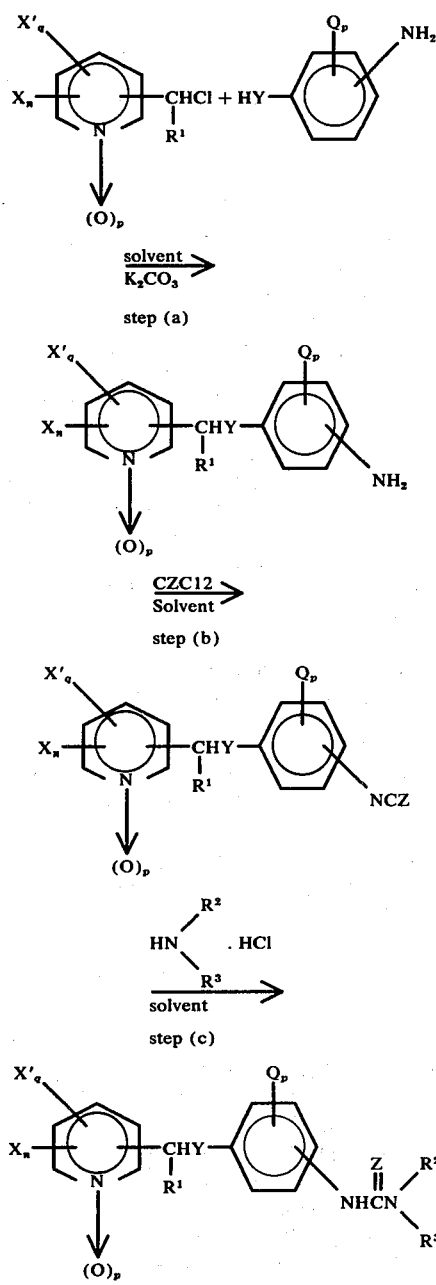

REACTION IV

Step (a) of Reaction IV is carried out in a manner analogous to the procedure set forth in Reaction I to obtain the corresponding amine intermediate. The amine intermediate is then reacted with phosgene or thiophosgene in the presence of toluene or other suitable inert solvent to form the corresponding novel isocyanate intermediate. The isocyanate intermediates are prepared (step b of Reaction IV) by first forming a solution of phosgene or thiophosgene in a solvent, such as toluene or the like, and then rapidly adding, with stirring, a solution of the amine starting material in toluene. The amine addition is regulated so as to maintain the temperature of the mixture at about 5° C. or less, with additional quantities of solvent being added if necessary. Following the completion of the amine addition, the reaction mixture is agitated and heated gradually until a temperature of from about 75° to about 95° C. is reached. The solvent carrier is then removed from the reaction mixture by evaporation under reduced pressure and the remaining residue taken up in hexane which is then cooled to crystallize the desired product. An excess of phosgene or thiophosgene, in a ratio of from about 3 to about 4 moles thereof per mole of amine reactant, is preferably employed in the reaction. During the reaction, excess phosgene can be removed by purging the reaction mixture with an inert gas, such as nitrogen.

The isocyanate intermediate thus obtained is reacted, in step c of Reaction II, with a selected substituted hydroxylamine salt in the presence of an inert solvent, such as one of these hereinbefore mentioned, to form the desired phenyl urea compound. The reaction is conducted under ambient atmospheric pressure at temperatures of from about 50° to about 100° C. Preferably, an actuating agent is employed to liberate the hydroxylamine from its acid salt as well as increase the adduction thereof with the isocyanate reactant. Representative actuating agents that can be employed include, for example, tertiary amines such as triethylamine and the like. The reactants are usually employed in stoichiometric proportions while an excess of the actuating agent is employed.

In carrying out the reaction, the isocyanate and substituted hydroxylamine reactants are contacted in the presence of a dry inert solvent containing the actuating agent. Representative solvents include, for example, pyridine, toluene or the like. The resulting reaction mixture is heated with stirring at a temperature within the above described range for a period of from about ¼ to about 2 or more hours. The reaction mixture is then stirred at ambient temperatures for a period of from about 1 to about 12 hours and then cooled and mixed with cold water. The resulting product precipitate is recovered and purified in typical procedures previously set forth.

The compounds of the present invention wherein T is

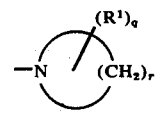

, hereinafter referred to as "carboxamide" products, are prepared by reacting an isocyanate intermediate (Reaction IV) with a selected piperidine or pyrrolidine reactant under conditions such as described in step (b) of Reaction II. Stoichiometric quantities of the reactants are usually employed.

In still other procedures, the foregoing phenylurea compounds of Reaction IV and the foregoing carboxamide products, especially the N-oxide derivatives thereof, are prepared by reacting an amino(thio)- phenol reactant with phosgene or thiophosgene, as in step (b) of Reaction IV, thereby obtaining a corresponding hydroxy- or mercapto- phenyliso(thio)cyanate reactant. Such phenyliso(thio)cyanate reactant can be reacted with a selected hydroxylamine reactant, as in step (c) of Reaction IV, to obtain a corresponding hydroxy- or mercapto- phenylurea intermediate which can be reacted with a haloalkylpyridine reactant or an N-oxide derivative thereof employing procedures analogous to those described in the alternative procedures following Reaction II. The phenyliso(thio)cyanate reactant can also be employed in the preparation of the foregoing carboxamide products and N-oxide derivatives thereof by reacting the same with a piperidine or pyrrolidine reactant, employing conditions analogous to those of step (b) in Reaction II. The thus-formed phenyl(pyrrolidine- or piperidine-)carboxamide intermediate is reacted an appropirate haloalkylpyridine reactant according to the appropriate alternative procedures set forth before Reaction III.

The compounds of the present invention wherein Y is —SO₂ and T is R³ are prepared by reacting a selected substituted acetamidobenzenesulfinic acid reactant with haloalkylpyridine reactant according to procedures employed in Reaction I. The corresponding pyridinylbenzenamine intermediates thereof can be prepared by treating the thus obtained acetamide compound with BF₃ employing the appropriate procedures set forth in Step (a) of Reaction II. The N-oxide derivatives of such benzenamine intermediates can be prepared employing the various alternative methods hereinbefore described. Such benzenamine intermediates can be reacted with (thio)phosgene to form a corresponding novel pyridinylphenyliso(thio)cyanate intermediate which is then reacted with an appropriate hydroxylamine reactant employing the procedures illustrated in steps (b) and (c) of Reaction IV above to obtain the desired phenylurea compound. The corresponding sulfonyl carboxamide compounds and N-oxide derivatives thereof are prepared by reacting the isocyanate intermediates with an appropriate piperidine or pyrrolidine reactant utilizing reaction conditions analogous to those set forth in step (b) of Reaction II and the foregoing described alternative procedures.

The following examples illustrate the present invention and the manner by which it can be practiced but as such, should not be construed as limitations upon the overall scope of the same.

EXAMPLE 1

N-(4-((3,6-dichloro-2-pyridinyl)methoxy)phenyl)-propanamide 3,6-Dichloro-2-chloromethylpyridine (5.17 grams; 0.026 mole) was dissolved in 20 milliliters (ml) of dimethylsulfoxide and a solution of p-phenol propionamide (4.96 grams; 0.03 mole) and sodium metal (0.69 grams; 0.03 mole) in 35 ml. of methanol added dropwise thereto over a period of about 45 minutes, with the reaction temperature of mixture increasing exothermically from ambient temperatures to about 35° C. Following the completion of the addition, the reaction mixture was distilled to remove the methanol and then poured over ice and allowed to stand for about 2 hours. The gummy solid formed upon standing was obtained by filtration and recrystallized from benzene. As a result of these operations, the desired N-(4-((3,6-dichloro-2-pyridinyl)methoxy)phenyl)propanamide compound was obtained as a crystalline solid having a melting point of 169°–171° C.

EXAMPLE 2

4-((3,6-dichloro-2-pyridinyl)methylthio)benzenamine p-Aminothiophenol (6.25 grams; 0.05 mole) was dissolved in 40 ml. of dimethylsulfoxide and powdered dry sodium hydroxide (2.0 grams; 0.05 mole) added thereto. The resulting mixture was warmed slightly, stirred and an additional 20 ml. of dimethylsulfoxide added thereto to clear the solution. A solution of 3,6-dichloro-2-chloromethylpyridine (8.6 grams, 0.05 mole) in 20 ml. of dimethylsulfoxide was added thereto slowly, with stirring, over a period of about one hour, The temperature of the reaction mixture increased to about 30°–45° C. during the addition. Following the completion of the addition, the reaction mixture was cooled and poured over ice and allowed to stand for about 15 hours. The aqueous layer was then decanted and the residue extracted with 5–500 ml. portions of hexane and the product precipitate recovered therefrom. Recrystallization of the precipitate from benzene gave the desired N-(4-((3,6-dichloro-2-pyridinyl)-methylthio) benzenamine compound as a crystalline solid having a melting point of 110°–111° C.

EXAMPLE 3

4((3,6-dichloro-2-pyridinyl)methoxy)benzenamine

N-(4-((3,6-Dichloro-2-pyridinyl)methoxy)phenyl-)acetamide (30.27 grams; 0.097 mole) was mixed with a 270 ml. solution of boron trifluoride-methanol (1 gram per 10 ml.) and the resulting reaction mixture refluxed for a period of 4 ½ hours. The reaction mixture was then diluted and cooled with ice water to a temperature of between about 0° to about 10° C. Concentrated ammonium hydroxide was added until the reaction mixture was basic. The reaction mixture was then extracted with portions of methylene chloride, the extracts combined and the solvent removed by evaporation. The residue thus obtained was extracted with five 500 ml. portions of hexane. The crystalline material which precipitated from the hexane mixture upon cooling was recovered by filtration. As a result of these operations, the desired 4-((3,6-dichloro-2-pyridinyl)-methoxy)benzenamine compound was recovered as a light yellow crystalline solid having a melting point of 74°–75° C.

EXAMPLE 4

3,6-dichloro-2-((4-isocyanatophenoxy)methyl)pyridine

Dry toluene (225 ml) was cooled to a temperature of from about 0° to 5° C. and a stream of phosgene gas passed therethrough until 17.4 grams had been absorbed. A solution of 4-((3,6-dichloro-2-pyridinyl)methoxy)benzenamine (15.8 grams; 0.058 mole) in 125 ml. of toluene was added portionwise thereto over a period of about 8 minutes while maintaining the reaction mixture temperature at about 2° to 5° C. The cloudy reaction mixture was then stirred for about 20 minutes with the temperature thereof slowly increasing as excess phosgene was purged from the reaction mixture with nitrogen. At a temperature of about 85° C., the reaction mixture became clear. The toluene solvent was then removed from the reaction mixture under reduced pressure and the residue obtained extracted with hexane. The yellow crystalline product recovered from the hexane extract upon cooling was identified as the desired 3,6-dichloro-2-((4-isocyanatophenoxy)methyl)pyridine compound and was found to have a melting point of 61.5°–62.5° C.

EXAMPLE 5

N'-(4-((3,6-dichloro-2-pyridinyl)methoxy)phenyl)-N-methoxy-N-methyl urea

Triethylamine (4.55 grams; 0.045 mole) was added to a solution of O,N-dimethylhydroxylamine hydrochloride (4.1 grams; 0.042 mole) in 40 ml. of dry pyridine. 3,6-dichloro-2-((4-isocyanatophenoxy)methyl)pyridine (12.4 grams; 0.042 mole) was added thereto and the resulting mixture heated for 20 minutes at about 60° C. The reaction mixture was then mixed with ice and the resulting precipitate recovered by filtration and recrystallized from a benzenehexane (90:10) mixture. As a result of such operations, the desired N'-(4-((3,6-dichloro-2-pyridinyl)methoxy)phenyl)-N-methoxy-N-methyl urea compound was recovered as a crystalline solid having a melting point of 152°–153.5° C.

EXAMPLE 6

N'-(4-((3,6-dichloro-2-pyridinyl)methoxy)phenyl)-N,N-dimethyl urea

Sodium metal (0.67 grams; 0.03 mole) was dissolved in 35 ml. of methanol and N,N-dimethyl-4-hydroxyphenyl urea (5.23 grams; 0.03 mole) was added to the sodium methoxide solution and the resulting mixture stirred until it became clear. The resulting phenolate solution was added portionwise over a period of about 90 minutes to a solution of 3,6-dichloro-2-chloromethylpyridine in 20 ml. of dimethylsulfoxide while maintaining the reaction at a temperature between from about 25° to about 50° C. The reaction mixture was then distilled to remove the methanol and the residue quenched over ice. The solid isolated by filtration was recrystallized from benzene. As a result of these operations, the desired N'-(4-((3,6-dichloro-2-pyridinyl)methoxy)phenyl)-N,N-dimethyl urea compound was recovered as a crystalline solid having a melting point of 161.5° to 162.5° C.

EXAMPLE 7

N'-(4-(((3,6-dichloro-2-pyridinyl)methyl)thio)phenyl)-N,N-dimethyl urea

A solution of 4-(((3,6-dichloro-2-pyridinyl)methyl)thio)benzenamine (10 grams; 0.035 mole) in 25 ml. of dry pyridine was prepared and dimethyl carbamoyl chloride (3.77 grams; 0.035 mole) added thereto while maintaining the temperature of the reaction mixture at 24°–45° C. The resulting reaction mixture was stirred at ambient temperatures for a period of about 15 hours and then mixed with ice and allowed to stand for a period of about two hours. The aqueous layer was decanted and the residue washed with water and recrystallized twice from ether. As a result of the above operations, the desired N'-(4-(((3,6-dichloro-2-pyridinyl)methyl)thio)phenyl)-N,N-dimethyl urea compound was recovered as a crystalline solid having a melting point of 112–113.5° C.

N'-(4-((6-chloro-2-pyridinyl)methoxy)phenyl)-N,N-dimethylurea;

N,N-dimethyl-N'-(4-((2-pyridinylmethyl)thio)phenyl)urea;

N,N-dimethyl-N'-(4-(2-pyridinylmethoxy)phenyl)urea;

N'-(4-(((6-chloro-2-pyridinyl)methyl)thio)phenyl)-N,N-dimethylthiourea;

N'-(4-((6-methyl-2-pyridinyl)methoxy)phenyl)-N,N-dimethylurea;

N'-(4-(((6-methyl-2-pyridinyl)methyl)thio)phenyl)-N,N-dimethylurea;

N'-(4-((4-amino-3,5,6-trichloro-2-pyridinyl)methoxy)phenyl)-N,N-dimethylthiourea;

N'-(4-(((6-iodo-2-pyridinyl)methoxy)-3-chlorophenyl)-N-butylurea-1-oxide;

N'-(4-(((6-bromo-2-pyridinyl)methyl)thio)-3-methylphenyl)-N,N-dibutylthiourea;

N'-(4-((6-fluoro-2-pyridinyl)-1-methylmethoxy)-3-bromophenyl)urea-1-oxide;

N'-(3-((6-(trifluoromethyl)-3-pyridinyl)methoxy)-4-ethylphenyl-N-methyl-N-propylurea;

N-butyl-N-methoxy-N'-(4-(((6-methylthio)-4-pyridinyl)-1-methylmethoxy)phenyl)urea-1-oxide;

N-butoxy-N'-(3-(((4-chloro-6-methyl-2-pyridinyl)methyl)thio)phenyl)-N-methylthiourea;

N'-(4-((4-cyano-6-methyl-2-pyridinyl)methoxy)-2-fluorophenyl)-N,N-dimethylurea-1-oxide;

N'-(4-(6-(trichloromethyl)-4-pyridinyl)methoxy)-phenyl)urea;

N'-(4-((1-(6-methoxy-4-pyridinyl)ethoxy)-3-chlorophenyl)-N-methoxy-N-methylurea-1-oxide;

N,N-dimethyl-N'-(4-(((3,4,5,6-tetrachloro-2-pyridinyl)methyl)thio)phenyl)thiourea;

N'-(4-(1-(3,5-dichloro-4,6-dimethyl-2-pyridinyl)ethylthio)-3-chlorophenyl)-N,N-dimethylurea;

N'-(4-((2,6-bis(trifluoromethyl)-4-pyridinyl)methoxy)phenyl)-N-methoxy-N-methylurea;

N'-(4-(3-chloro-4,6-bis(trifluoromethyl)-2-pyridinyl)methyl)thio)phenyl)-N-ethoxy-N-methylurea-1-oxide;

N'-(4-(1-(3,4,5,6-tetrabromo-2-pyridinyl)ethoxy)-phenyl)-N,N-dimethylthiourea;

N-(4-((4-chloro-6-methylthio-2-pyridinyl)methoxy)-3-chlorophenyl)-2,5-dimethyl-1-pyrrolidinecarboxamide;

N-(4-(((3,4,5,6-tetrachloro-2-pyridinyl)methyl)thio)-3-methylphenyl)-2,6-dimethyl-1-piperidinethiocarboxamide;

N-(4-(1-(4-chloro-6-(trifluoromethyl)-2-pyridinyl)ethoxy)phenyl)-1-pyrrolidinecarboxamide;

N-(3-(1-(6-bromo-4-cyano-2-pyridinyl)ethylthio)-phenyl)-1-piperidinecarboxamide;

N-(4-((2,6-bis(trifluoromethyl)-4-pyridinyl)methoxy)-3-ethylphenyl)-2,5-dimethyl-1-pyrrolidinecarboxamide;

N'-(4-((4-amino-3,5,6-trichloro-2-pyridinyl)methoxy)phenyl)-N,N-dimethylthiourea;

N'-(4-(((6-amino-4-methyl-2-pyridinyl)methyl)thio)-3-ethylphenyl)-N-methoxy-N-methylurea-1-oxide;

N'-(4-(1-(4-amino-3,5-dichloro-6-methyl-2-pyridinyl)ethoxy)phenyl)-N,N-dimethylthiourea;

N-(4-((4-amino-3,5-dimethyl-2-pyridinyl)methoxy)-3-fluorophenyl)-2,5-dimethyl-1-pyrrolidinecarboxamide;

N'-(4-(((5-chloro-2,6-dimethoxy-2-pyridinyl)methyl)thio)phenyl)-N,N-dipropylurea-1-oxide;

N'-(4-((2-cyano-6-(trifluoromethyl)-4-pyridinyl)methoxy)phenyl)-N-methoxy-N-methylthiourea;

N'-(4-(((4,6-diamino-3-chloro-2-pyridinyl)methyl)thio)-2-chlorophenyl)-N-t-butoxy-N-methylurea;

N-(4-((3,5-dichloro-6-methylthio-2-pyridinyl)methoxy)phenyl)-1-pyrrolidinecarboxamide;

N-(3-(1-(4-pyridinyl)ethylthio)phenyl)-2,5-dimethyl-1-pyrrolidinecarboxamide;

N'-(3-(1-(6-chloro-3-pyridinyl)ethoxy)phenyl)-N-methyl-N-methoxythiourea; and

N'-(4-((3,5-dichloro-6-(trichloromethyl)-2-pyridinyl)methoxy)-3-chlorophenyl)-N,N-dimethylurea.

The novel amine, isocyanate and acetamide intermediates which are employed, inter alia, to prepare the foregoing are readily apparent in view of the specific enumerated compounds. Such benzenamine intermediates are of the formula represented in Reaction Sequences II, III and IV of the specification and are prepared in accordance with the teachings of the specification and the foregoing Examples 2 and 3.

The nomenclature for such compounds is as set forth in such examples. The novel isocyanate intermediates employed to prepare, inter alia, the above-enumerated compounds are likewise readily apparent in view of the aboveenumerated compounds as well as the benzenamine intermediates from which the isocyanate intermediates are themselves prepared. Such isocyanate intermediates correspond to the general formula represented in reaction sequence IV set forth hereinbefore. Such novel intermediates are prepared according to the teachings of the specification and representative example 4, wherein the representative nomenclature for such compounds is also set forth. The novel acetamide compounds which are useful as intermediates in preparing the corresponding benzenamine and isocyanate intermediates, include those which correspondingly are used in preparing the compounds enumerated above. Such acetamide compounds correspond to the formula set forth in reaction sequence I and are prepared according to the teachings of the specification and Example 1, wherein the nomenclature for such compounds is set forth.

The compounds of the present invention have been found to be suitable for use in methods for the pre- and post- emergent control of weeds or other unwanted vegetation. For such uses, unmodified active ingredients of the present invention can be employed. However, the present invention embraces the use of a herbicidally-effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water or water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, keiselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 0.05 to about 95 percent by weight or more. Concentrations of from about 0.1 to about 50 weight percent are often employed. In dusts or dry formulations, the concentration of the active ingredient can be from about 0.05 to about 95 weight percent or more; concentrations of from about 0.1 to about 50 weight percent are often conveniently employed. In compositions to be employed as concentrates, the active ingredient can be present in a concentration of from about 1 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to be contacted with the toxic active ingredient. Thus, it is to be understood that all of the active ingredients of the invention and compositions containing the same may not be equally effective at similar concentrations or against the same plant species. Generally, compositions containing the active ingredients of this invention are usually applied at a rate sufficient to provide from about 2 to about 25 lbs. of the active ingredient per acre. However, in some instances, lower dosages may be utilized while higher dosages may be necessary in other instances. In view of the foregoing and following disclosures, one skilled in the art can readily determine the optimum rate to be applied in any particular case.

So as to illustrate the phytotoxic properties of the active ingredients of the present invention, a group of controlled greenhouse experiments is described. In pre-emergence operations, seeds of selected species are planted in seedbeds and, while exposed, sprayed with a given volume of a solution containing a predetermined amount of the candidate active ingredient to provide the dosage rate desired. Such compositions are prepared by mixing the selected active ingredient and an emulsifier or dispersant with water. The seeds are then covered with a layer of soil and maintained under conditions conducive to growth. A portion of the planted seedbeds are left untreated to provide controls for comparative purposes. All seedbeds are watered from below as needed. About 14 days after seeding and treating, the effect of each of the test ingredients on the seeds is evaluated by a comparison with the control seedbeds.

In post-emergence operations, various species of plants are seeded in beds of good agricultural soil. After the plants have emerged and grown to a height of from about 2 to 6 inches, certain of the plants are sprayed to run-off with a given volume of a composition prepared as set forth above. Other plants are left untreated to provide comparative controls. All plants are maintained as above for a period of about 14 days and then evaluated to determine the effect of each test ingredient.

In representative general pre-emergence operations, each of the N'-(4-(((3,6-dichloro-2-pyridinyl)methyl)thio)phenyl)-N,N-dimethylurea (Compound No. 1); N'-(4-(2-pyridinylmethoxy)phenyl)-N,N-dimethylurea (Compounds No. 2); N'-(4-((6-chloro-2-pyridinyl)methoxy)phenyl)-N,N-dimethylurea (Compound No. 3); N'-(4-((3,6-dichloro-2-pyridinyl)methoxy)phenyl)-N-methoxy-N-methylurea (Compound No. 4); N'-(4-(((2-pyridinyl)methyl)thio)phenyl)-N,N-dimethylurea (Compound No. 5); N'-(4-((3,6-dichloro-2-pyridinyl)methoxy)phenyl)-N,N-dimethylurea (Compound No. 6); and N'-(4-(((6-chloro-2-pyridinyl)methyl)thio)phenyl)-N,N-dimethylurea (Compound No. 7) was found to give from substantial (70%) to complete (100%) control of the growth of the seeds of crabgrass, barnyard grass, wild oat and yellow foxtail species when contacted with a sufficient amount of a composition containing one of the above-named active ingredients to provide an application rate of about 10 pounds of the active ingredient per acre.

In additional representative pre-emergence operations, N'-(4-((6-methyl-2-pyridinyl)methoxy)phenyl)-N,N-dimethylurea (Compound No. 8); N'-(4-(((6-methyl-2-pyridinyl)methyl)thio)phenyl)-N,N-dimethylurea (Compound No. 9); and compounds No. 1, No. 2, No. 4, No. 6 and No. 7 were each found to give from substantial to complete control of the growth of pigweed seeds at an application rate of about 10 pounds of the active ingredient per acre.

In additional representative pre-emergence operations, N'-(4-((4-amino-3,5,6-trichloro-2-pyridinyl)methoxy)phenyl)-N,N-dimethylurea (Compound No. 10) was found to give from substantial to complete control of the growth of crabgrass, annual morning glory and velvet leaf seeds at an application rate of about 10 pounds per acre.

In other pre-emergence operations, Compound No. 4 was found to selectively give from substantial to complete control of wildoats, yellow foxtail, barnyard grass, crabgrass, pigweed and velvet leaf seeds without inhibiting the growth of cotton seeds at an application rate of 10 pounds per acre.

In post-emergence operations, compound 10 was found to give from about 95 to about 100% control of the growth of yellow foxtail, barnyard grass, annual morning glory and velvet leaf plants at an application rate of about 10 pounds per acre.

In additional post-emergence operations, each of compounds 1–9 above were found to give from substantial to complete control of the growth of yellow foxtail, barnyard grass, crabgrass and pigweed plants at an application rate of about 10 pounds per acre.

In other post-emergence operations, compound 10 was found to give substantial control of the growth of pigweed and barnyard grass plants at an application rate of about 1.25 pounds per acre.

STARTING MATERIALS

The haloalkylpyridine reactants employed as starting materials in the present invention are readily available or can be prepared according to known procedures or procedures analogous thereto. For example, the 3,6-dichloro-2-chloromethyl pyridine is prepared by converting the methyl ester of 3,6-dichloropyridine carboxylic acid to the corresponding alcohol by reaction with NaBH4 and methanol in the presence of water.

The 3,6-dichloro-2-hydroxymethylpyridine product is then reacted with thionyl chloride in the presence of a catalytic amount of pyridine hydrochloride at temperatures of about 65° C. for a period of from about 15 to about 20 minutes. The thionylchloride is then removed by evaporation and the residue cooled, mixed with ice and then extracted with hexane. The desired 3,6-dichloro-2-chloromethyl pyridine reactant is obtained as a light yellow oil. Other haloalkyl pyridine starting materials can be prepared in an analogous manner.

The acetamide (thio)phenol, urea(thio)phenol, and acetamidobenzene sulfinic acid reactants are also readily available or can be prepared according to methods known in the literature. For example, p-hydroxypropionanilide is prepared by reacting p-aminophenol with 2 molar equivalents of propionyl chloride and 2 molar equivalents of triethylamine in the presence of benzene under ambient temperature conditions. The reaction mixture is filtered and distilled to remove the solvent and the residue extracted with methylene chloride. Upon cooling, the crystalline material found is recovered by filtration, recrystallized from benzene-hexane mixture, and then dissolved in 2B Alcohol and aqueous sodium hydroxide added thereto. The resulting reaction mixture is refluxed for about 10 minutes and then distilled to remove methanol. The reaction mixture is then diluted with water, acidified with concentrated hydrochloric acid. The resulting solid precipitate is recovered by filtration, mixed with aqueous sodium hydroxide and filtered to remove insolubles. The filtrate is then acidified with concentrated hydrochloric acid and the resulting precipitate recovered. As a result of these operations, the p-hydroxy propionanilide starting material is obtained as a crystalline solid having a melting point of 169°–171° C.

In another representative operation, N,N-dimethyl-4-hydroxyphenylurea is obtained in a representative operation by adding dimethylcarbamoyl chloride to p-aminophenol in dry pyridine at temperatures of from about 25°–50° C. The addition is carried out over a period of about 30 minutes, after which the reaction mixture is stirred at ambient temperatures for a period of about 15 hours. The reaction mixture is then mixed with ice and the resulting red-brown solid formed upon standing is recovered by filtration. As a result of the above operations, the desired starting material is obtained as a crystalline solid having a melting point of 178°–179° C.

The hydroxylamine, carbamoyl halide, aminophenol, pyrrolidine and piperidine reactants employed in the present invention are known and are readily available or can be prepared according to known procedures or in operations analogous thereto.

Although the invention is described with respect to specific embodiments and modifications, the details thereof are not to be construed as limitations except to the extent indicated in the following claims.

I claim:

1. The method of controlling undesired plant growth which comprises applying to plants and/or their habitats a herbicidally-effective amount of a compound of the formula:

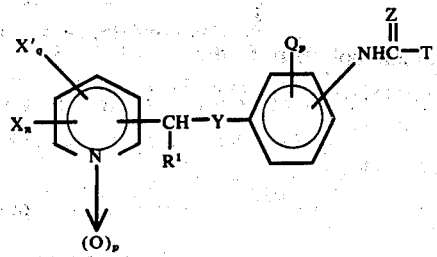

wherein

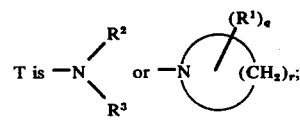

each X independently represents bromo, chloro, fluoro or iodo;
each X' independently represents trichloromethyl, $NH_2$, trifluoromethyl, cyano, methyl, methylthio or methoxy;
n represents an integer of 0 to 4, inclusive;
each q independently represents an integer of 0 to 2, inclusive;
each p independently represents an integer of 0 or 1;
r represents an integer of 4 to 5;
each $R^1$ is hydrogen or methyl;
Y is a chalcogen of atomic number 8 to 16, inclusive or —SO2;
Q is methyl, ethyl or halo;
Z is a chalcogen of atomic number 8 to 16, inclusive;
$R^2$ represents hydrogen, alkyl of from 1 to 4 carbon atoms, inclusive or an alkoxy group of from 1 to 4 carbon atoms, inclusive; and
$R^3$ represents an alkyl group of from 1 to 4 carbon atoms, inclusive.

2. The method of claim 1 wherein q is at least one and n is zero.

3. The method of claim 1 wherein n is at least one and q is zero.

4. The method of claim 1 wherein n is 1, R is hydrogen and X is substituted in the 6 -ring position.

5. The method of claim 1 wherein T is

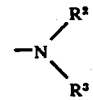

6. The method of claim 5 wherein the compound is N'-(4-((6-chloro-2-pyridinyl)methoxy)phenyl)-N,N-dimethylurea.

7. The method of claim 5 wherein the compound is N,N-dimethyl-N'-(4-((2-pyridinylmethyl)thio)phenyl)urea.

8. The method of claim 5 wherein the compound is N,N-dimethyl-N'-(4-(2-pyridinylmethoxy)phenyl)urea.

9. The method of claim 5 wherein the compound is N'-(4-((6-chloro-2-pyridinyl)methyl)thio)phenyl)-N,N-dimethylthiourea.

10. The method of claim 5 wherein the compound is N'-(4-((6-methyl-2-pyridinyl)methoxy)phenyl)-N,N-dimethylurea.

11. The method of claim 5 wherein the compound is N'-(4-((6-methyl-2-pyridinyl)methyl)thio)phenyl)-N,N-dimethylurea.

12. The method of claim 5 wherein the compound is N'-(4((4-amino-3,5,6-trichloro-2-pyridinyl)methoxy)-phenyl)-N,N-dimethylthiourea.

13. The method of claim 5 wherein the compound is N'-(4-(((6-iodo-2-pyridinyl)methoxy)-3-chlorophenyl)-N-butylurea1-oxide.

14. The method of claim 5 wherein the compound is N'-(4-((6-bromo-2-pyridinyl)methyl)thio)-3-methylphenyl)-N,N-dibutylthiourea.

15. The method of claim 5 wherein the compound is N'-(4-((6-fluoro-2-pyridinyl)-1-methylmethoxy)-3-bromophenyl)-urea-1-oxide.

* * * * *

UNITED STATES PATENT AND TRADEMARK OFFICE
CERTIFICATE OF CORRECTION

PATENT NO. : 4,028,092
DATED : June 7, 1977
INVENTOR(S) : Alin H. Gulbenk

It is certified that error appears in the above-identified patent and that said Letters Patent are hereby corrected as shown below:

Column 1 between lines 6 - 15 the title CROSS-REFERENCE TO RELATED APPLICATION and the paragraph following has been duplicated. Delete the second occurrence of the title and the paragraph following.

Column 1, line 18, "pyridinylalkyoxy-," should read --pyridinylalkoxy-,--.

Column 2, line 22, "term" should read --terms--.

Column 2, line 49, "In yet another embodiment," should read --In yet another preferred embodiment,--.

Column 4, line 2, "appropriated" should read --appropriately.

Column 9, line 27, "appropirate" should read --appropriate--.

Column 10, line 24 "hour," should read --hour.--.

Column 12, line 29, "ethylphenyl-N-methyl-N-propylurea;" should read --ethylphenyl)-N-methyl-N-propylurea;--.

Column 13, line 32, "aboveenumerated" should read --above-enumerated--.

Column 16, line 7, "(Compounds" should read --(Compound--.

UNITED STATES PATENT AND TRADEMARK OFFICE
CERTIFICATE OF CORRECTION

PATENT NO. : 4,028,092
DATED : June 7, 1977
INVENTOR(S) : Alin H. Gulbenk

It is certified that error appears in the above-identified patent and that said Letters Patent are hereby corrected as shown below:

Column 18, Claim 1, line 29, "4 to 5;" should read --4 or 5;--.

Column 18, Claim 1, line 32, "-SO2;" should read -- -$SO_2$;--.

Column 19, Claim 11, line 1, "methodof" should read --method of--.

Column 19, Claim 12, line 6, "N'-(4((4-amino-3,5,6-trichloro-2-pyridinyl)methoxy)-" should read --N'-(4-((4-amino-3,5,6-trichloro-2-pyridinyl)methoxy)- --.

Column 20, line 2, "phenyl)-N-butylureal-oxide." should read --phenyl)-N-butylurea-1-oxide.--.

Signed and Sealed this

First Day of November 1977

[SEAL]

Attest:

RUTH C. MASON
Attesting Officer

LUTRELLE F. PARKER
Acting Commissioner of Patents and Trademarks